US011241292B1

(12) United States Patent
Burmeister et al.

(10) Patent No.: US 11,241,292 B1
(45) Date of Patent: Feb. 8, 2022

(54) PORTABLE MEDICAL TREATMENT KIT

(71) Applicants: Sonja Burmeister, Coopersburg, PA (US); Tanja Ewing, Lansdale, PA (US)

(72) Inventors: Sonja Burmeister, Coopersburg, PA (US); Tanja Ewing, Lansdale, PA (US)

( * ) Notice: Subject to any disclaimer, the term of this patent is extended or adjusted under 35 U.S.C. 154(b) by 0 days.

(21) Appl. No.: 17/009,197

(22) Filed: Sep. 1, 2020

(51) Int. Cl.
*A61B 50/31* (2016.01)
*A45C 11/00* (2006.01)
*A61B 50/30* (2016.01)

(52) U.S. Cl.
CPC .............. *A61B 50/31* (2016.02); *A45C 11/00* (2013.01); *A45C 2011/007* (2013.01); *A61B 2050/3008* (2016.02); *A61B 2050/311* (2016.02)

(58) Field of Classification Search
CPC .... A61B 50/31; A45C 2011/007; A45C 11/00
USPC ...................................... 206/570, 223, 459.1
See application file for complete search history.

(56) References Cited

U.S. PATENT DOCUMENTS

| | | | | |
|---|---|---|---|---|
| 5,186,900 | A * | 2/1993 | Jensen ................. | A61B 10/007 422/550 |
| 7,565,979 | B1 * | 7/2009 | Gibson ..................... | A61J 7/04 206/363 |
| 7,921,583 | B2 * | 4/2011 | Londino ............... | G09F 3/0288 40/310 |
| 7,926,850 | B1 * | 4/2011 | Muncy .................... | B42F 7/065 283/70 |
| 2004/0195135 | A1 * | 10/2004 | Seamon ................. | A45C 13/02 206/459.1 |
| 2006/0289329 | A1 * | 12/2006 | Miller .................. | A45C 7/0054 206/570 |
| 2007/0095707 | A1 * | 5/2007 | Yahiel .................. | B65D 23/085 206/459.5 |
| 2007/0194128 | A1 * | 8/2007 | Coe ........................ | A45C 11/00 235/486 |
| 2008/0029410 | A1 * | 2/2008 | Dodsworth ............. | B42F 13/00 206/223 |
| 2008/0105328 | A1 * | 5/2008 | Desmond ................. | A45F 5/00 141/2 |
| 2010/0206751 | A1 * | 8/2010 | Wessel ............... | A61B 5/14532 206/38 |
| 2012/0061268 | A1 * | 3/2012 | Turner ..................... | A45F 5/02 206/232 |
| 2012/0305177 | A1 * | 12/2012 | Simmons .................. | G09F 3/10 156/247 |
| 2013/0139298 | A1 * | 6/2013 | Crump .................. | A41D 27/20 2/247 |

(Continued)

*Primary Examiner* — Rafael A Ortiz

(57) ABSTRACT

A portable medical kit is for treatment of at least one medical condition having first and second levels of severity and includes a portable case having an interior chamber and at least two medicine holders each configured to retain a separate one of a first medicine and a second medicine within the chamber or at least one medicine holder configured to retain both of the first and second medicines within the chamber. A sheet retainer is configured to couple at least one treatment instruction sheet with the case. Further, a first visual indicator is attachable to the first medicine and a second visual indicator is attachable to the second medicine, the second indicator being readily visually distinguishable from the first indicator. Alternatively, the kit includes instructions to form the first indicator and the second indicator.

14 Claims, 9 Drawing Sheets

(56) References Cited

U.S. PATENT DOCUMENTS

2013/0233741 A1* 9/2013 Caruth .................. A45C 5/005
              206/232
2017/0340403 A1* 11/2017 Roberts-Monteleone ..................
              A61K 31/426

* cited by examiner

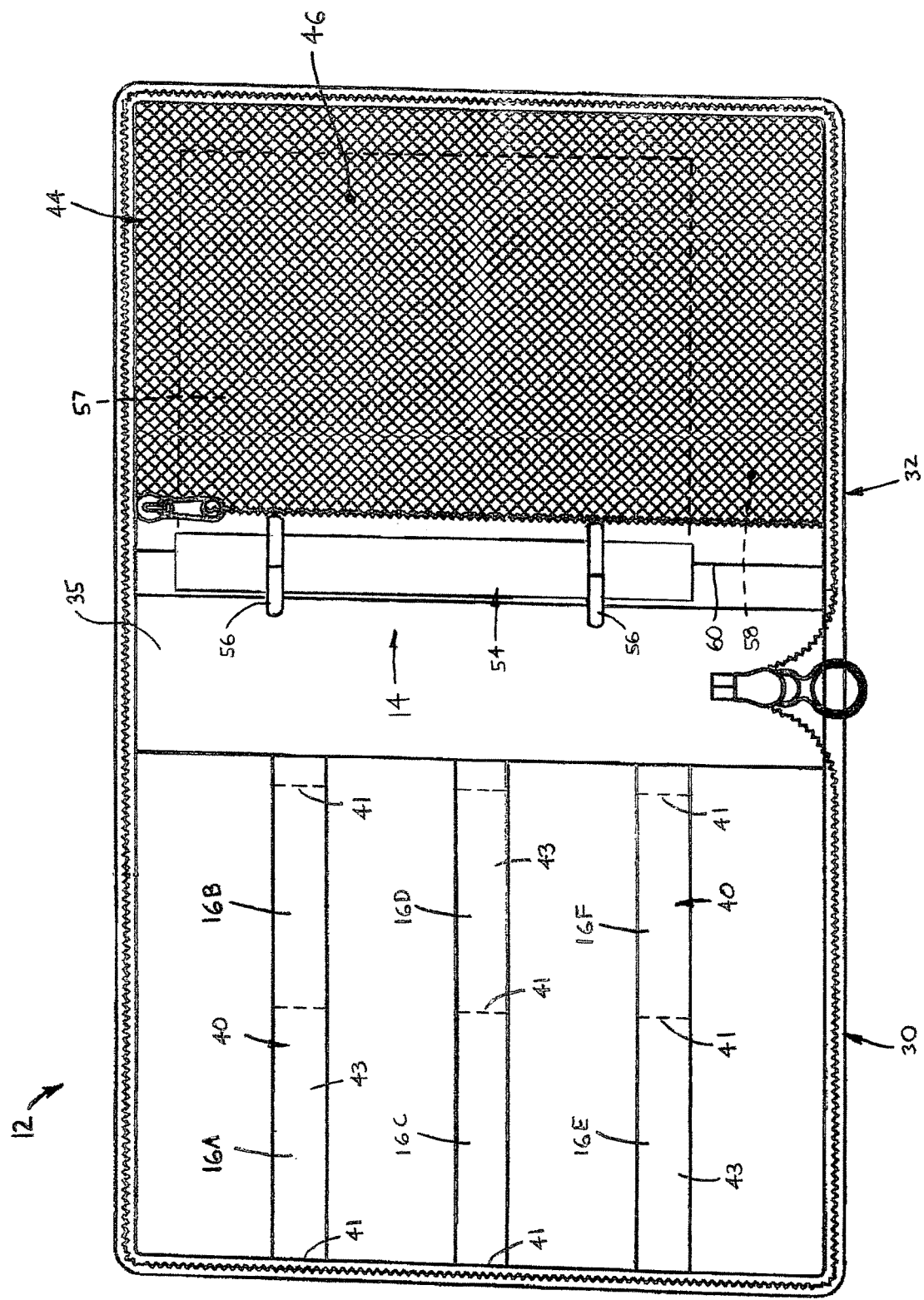

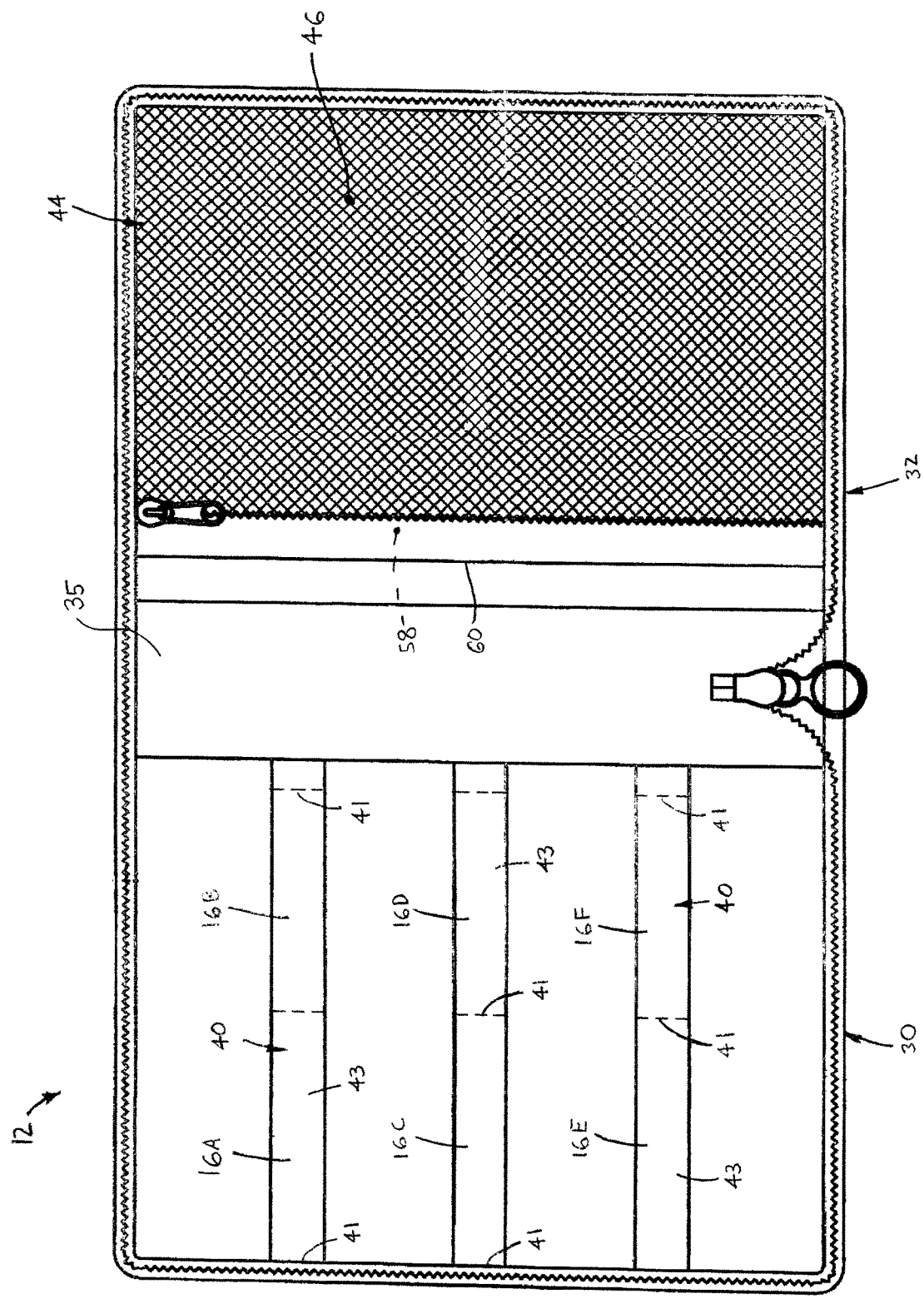

PORTABLE MEDICAL TREATMENT KIT

BACKGROUND OF THE INVENTION

The present invention relates to medical devices, and particularly to a medical treatment kit for containing medicine for treating one or more conditions.

Containers for medicines are known and come in a variety of forms, such as relatively small cases sized to be hand-held or larger cases or containers that may be either hand-held or wheeled. Such containers typically include one or more retainers or holders for securing the medicine(s) within the container.

SUMMARY OF THE INVENTION

The present invention is a portable medical kit for treatment of at least one medical condition having first and second levels of severity. The treatment kit comprises a portable case having an interior chamber and at least two medicine holders each configured to retain a separate one of a first medicine and a second medicine or at least one medicine holder configured to retain both of the first and second medicines. A sheet retainer is configured to couple at least one treatment instruction sheet with the case. The kit either includes a first visual indicator attachable to the first medicine and a second visual indicator attachable to the second medicine, the second indicator being readily visually distinguishable from the first indicator, or is provided with instructions to form the first indicator and the second indicator.

BRIEF DESCRIPTION OF THE SEVERAL VIEWS OF THE DRAWINGS

The foregoing summary, as well as the detailed description of the preferred embodiments of the present invention, will be better understood when read in conjunction with the appended drawings. For the purpose of illustrating the invention, there is shown in the drawings, which are diagrammatic, embodiments that are presently preferred. It should be understood, however, that the present invention is not limited to the precise arrangements and instrumentalities shown. In the drawings:

FIG. 8 is another front plan view of the treatment kit showing a preferred structure of a binder sheet retainer; and FIG. 9 is a front plan view of an alternative construction of the case, shown with a different structure of a sheet retainer

DETAILED DESCRIPTION OF THE INVENTION

Figure 1:
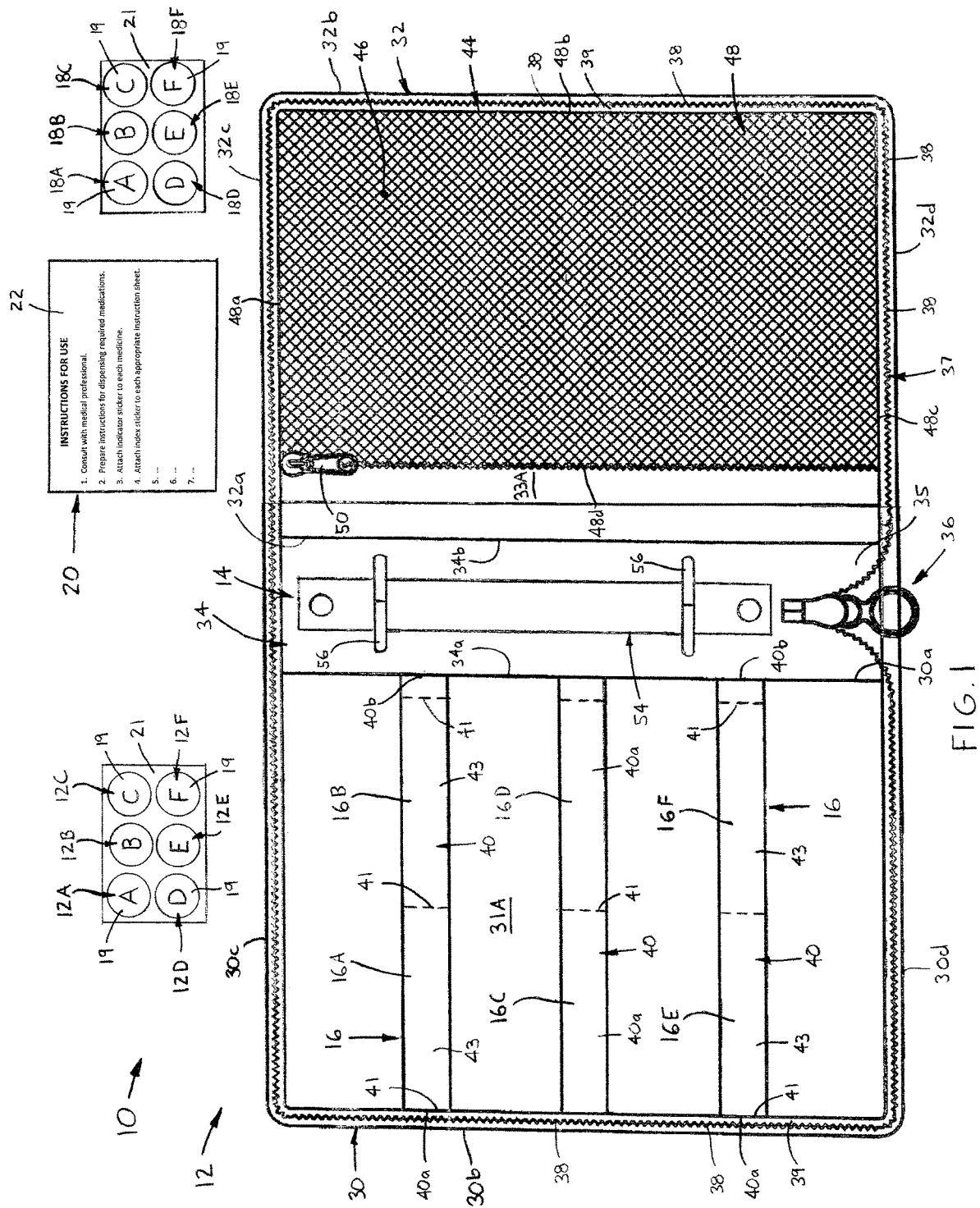
FIG. 1 is front plan view of a treatment kit in accordance with the present invention, shown in an open configuration.

Certain terminology is used in the following description for convenience only and is not limiting. The words "inner", "inwardly" and "outer", "outwardly" refer to directions toward and away from, respectively, a designated centerline or a geometric center of an element being described, the particular meaning being readily apparent from the context of the description. Further, as used herein, the words "connected" and "coupled" are each intended to include direct connections between two members without any other members interposed therebetween and indirect connections between members in which one or more other members are interposed therebetween. The terminology includes the words specifically mentioned above, derivatives thereof, and words of similar import.

Referring now to the drawings in detail, wherein like numbers are used to indicate like elements throughout, there is shown in FIGS. 1-9 a portable medical treatment kit 10 for treatment of at least one medical condition, e.g., an allergic reaction, asthma attack, heart condition, etc., having at least first and second levels of severity, and possibly three or more levels depending upon the particular condition. The treatment kit 10 is particularly well suited for use by an adult caregiver of children or the elderly, such as a daycare worker, a teacher, a sitter, a healthcare worker, etc., who may not be familiar with the particular medical needs of a child/infirm adult for whom the kit 10 is provided. The treatment kit 10 basically comprises a portable case 12 for containing two or more medicines M, specifically at least first and second medicines $M_1$, $M_2$, respectively, first and second visual indicators 12A, 12B, respectively and at least one instruction sheet retainer 14. More specifically, the case 12 has an interior chamber $C_C$ and at least two medicine holders 16A, 16B each configured to retain a separate one of a first medicine $M_1$ and a second medicine $M_2$ within the chamber $C_C$, or at least one medicine holder 16 configured to retain both of the first and second medicines $M_1$, $M_2$ within the chamber $C_C$. The medicines M may be contained within a pill bottle 1, a liquid medicine bottle 2, an asthma inhaler 3, an injector 4 (e.g., an epinephrine injector such as an AUVIQ® or EpiPen®, or any other appropriate container or dispenser capable of containing medicine. The first visual indicator 12A is attachable to the first medicine $M_1$ and the second visual indicator 12B is attachable to the second medicine $M_2$. The second indicator 12B is readily visually distinguishable from the first indicator 12A, and vice-versa, such that the correct medicine $M_1$ or $M_2$ may be readily selected by a user of the kit 10 (using an appropriate treatment instruction sheet as discussed below) under an urgent or critical situation such as an asthma attack, an allergic reaction, etc. Further, the sheet retainer 14 is configured to couple or connect at least one treatment instruction sheet $S_1$ with the case 12.

Preferably, the treatment kit 10 further comprises a first index 18A corresponding to the first indicator 12A, and thus the first medicine $M_1$, and a second index 18B corresponding to the second indicator 12B and thereby the second medicine $M_2$. The first index 18A is attachable to the instruction sheet $S_1$ and the second index 18B is attachable to either the same instruction sheet $S_1$ or to another instruction sheet $S_2$, for reasons described below. However, the kit 10 may be provided without any indices for attachment to the instruction sheet(s) $S_1$, $S_2$, etc., and instead only have written instructions to administer the visually marked medicines $M_1$, $M_2$, etc., for example "Give child medicine with red sticker when suffering hives", etc.

Figure 4:
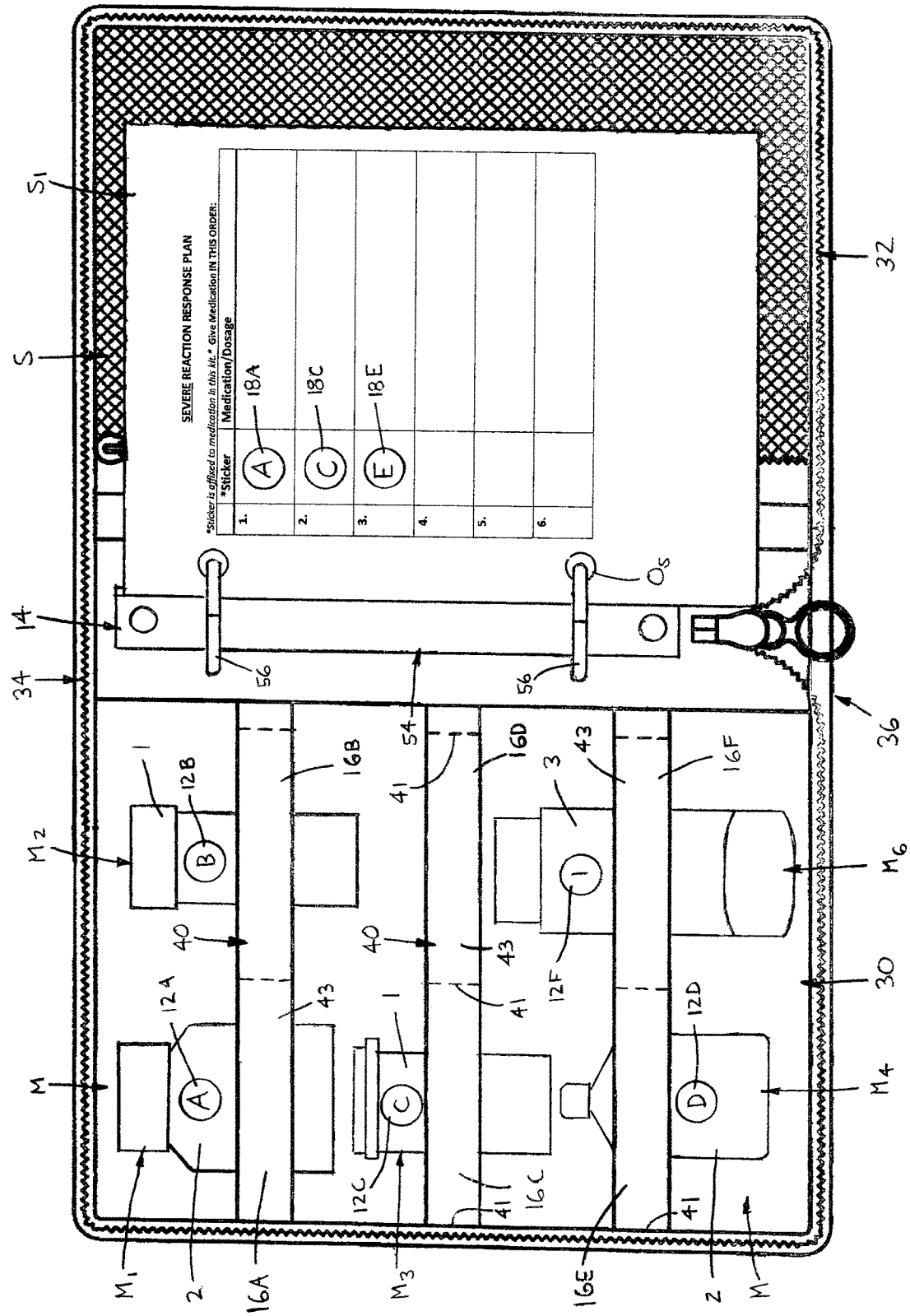
FIG. 4 is a front plan view of the treatment kit in an open configuration, shown with contained medicines and with a first instruction sheet.
Figure 5:
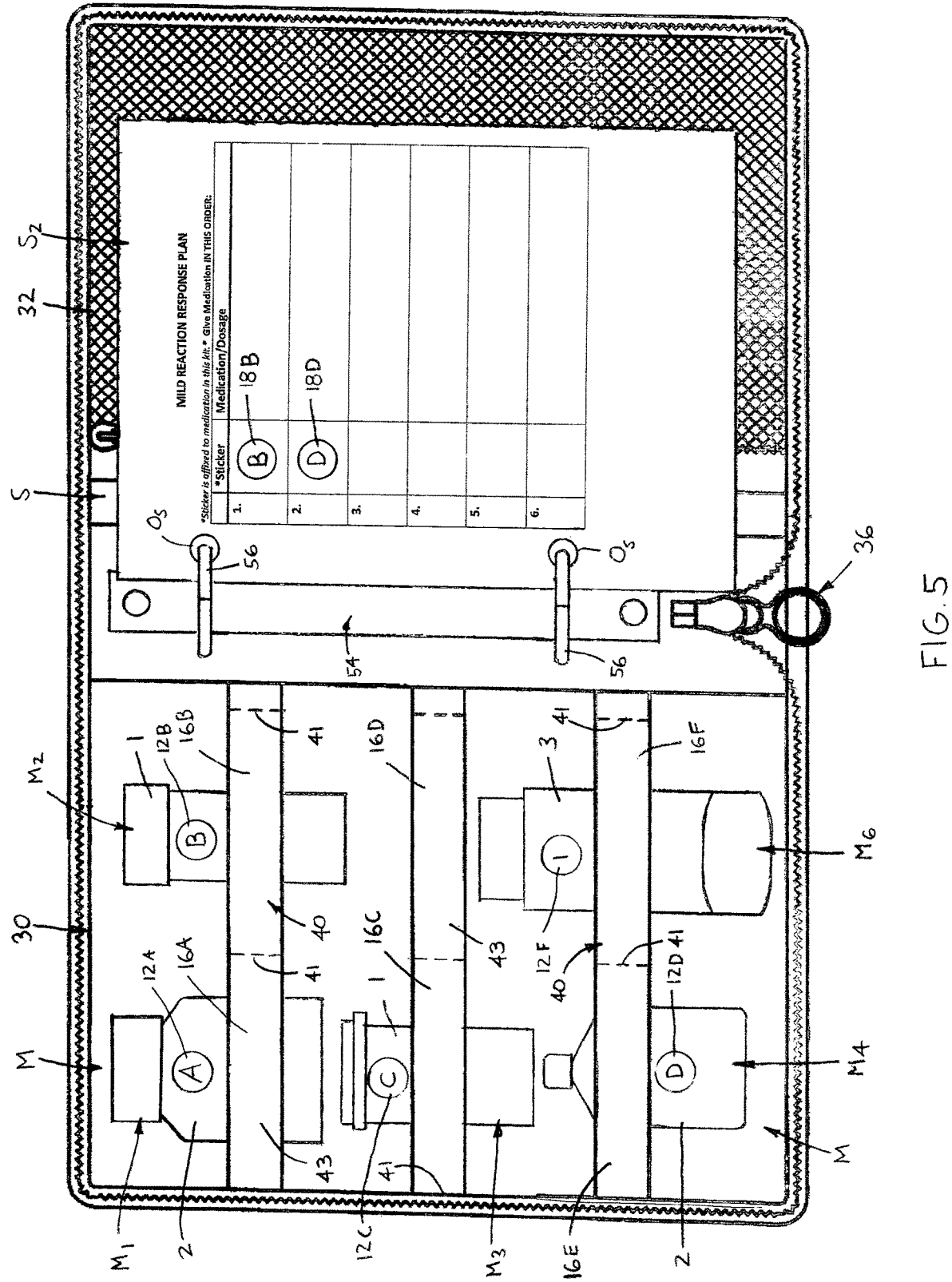
FIG. 5 is another front plan view of the treatment kit in the open configuration, shown with contained medicines and with a second instruction sheet.
Figure 6:
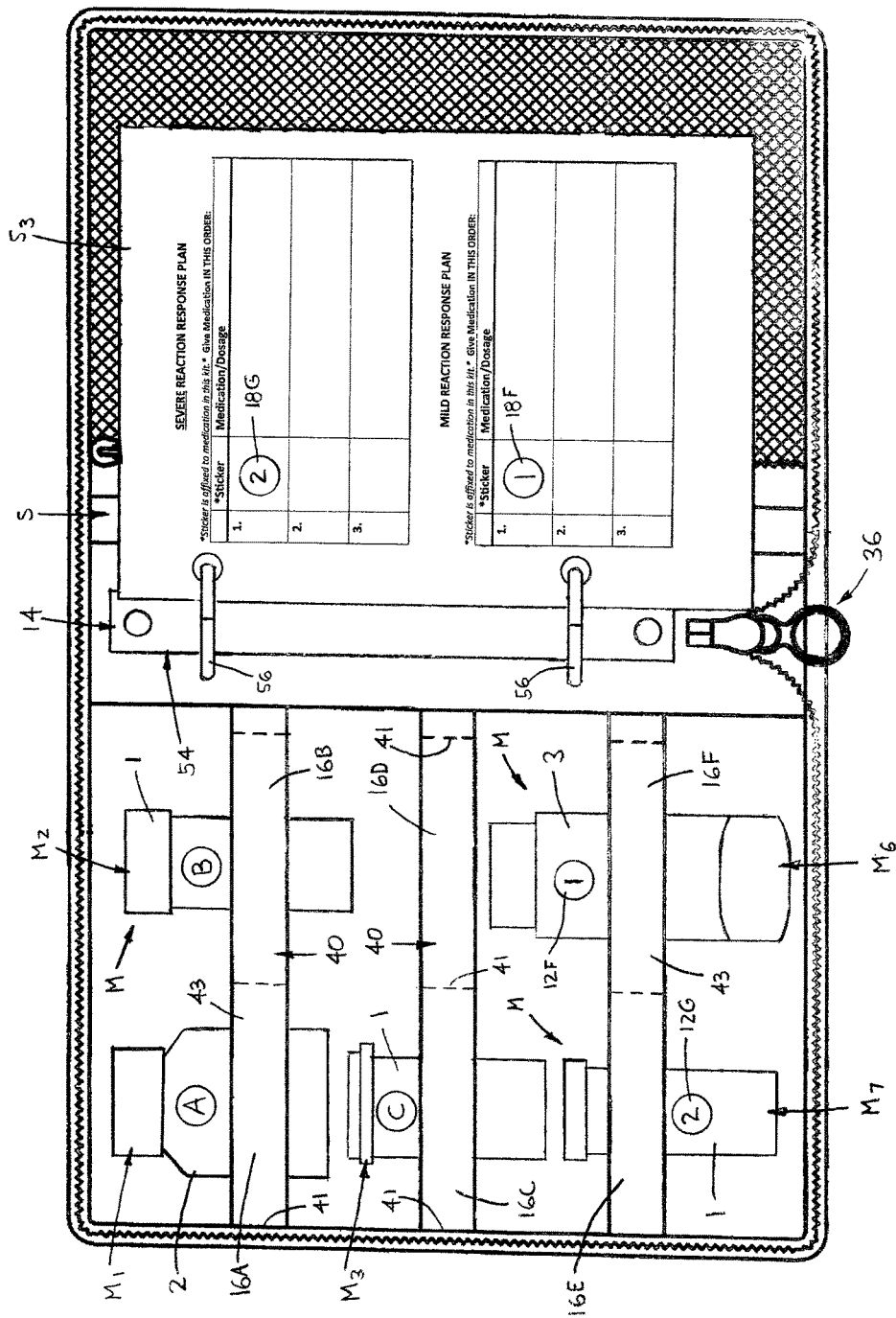
FIG. 6 is yet another front plan view of the treatment kit in the open configuration, shown with contained medicines and with a third instruction sheet.
Figure 7:
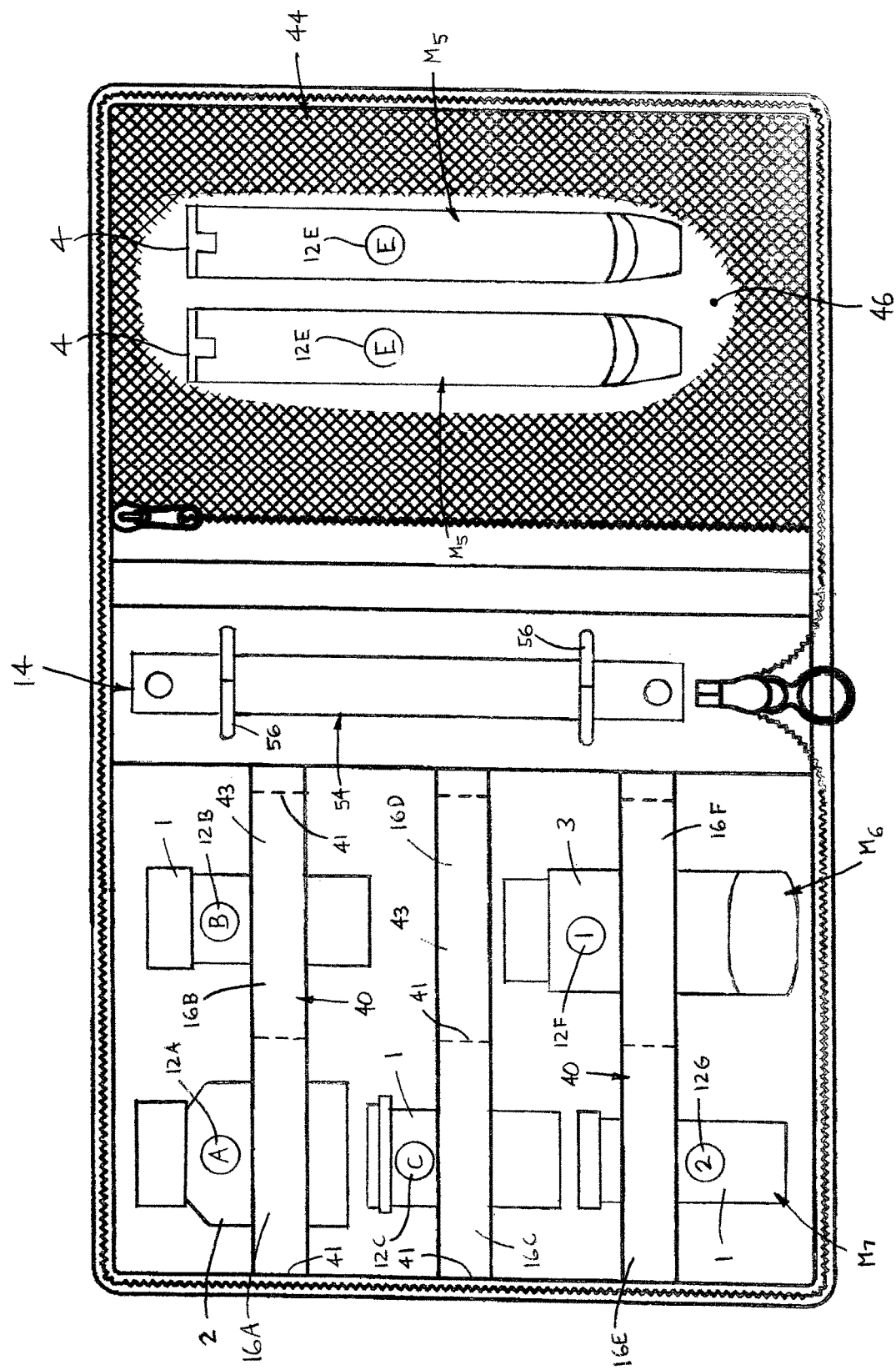
FIG. 7 is a further front plan view of the treatment kit, shown without any instruction sheet and with a broken-away panel to show the interior of a compartment.

Further, the treatment kit 10 preferably further comprises the at least one treatment instruction sheet $S_1$, preferably a plurality of treatment instruction sheets $S_1$, $S_2$, $S_3$, etc., each coupleable with the sheet retainer 14 and preferably including pre-printed blank lines, blank tables, etc. as discussed in further detail below. Each instruction sheet $S_1$, $S_2$, etc. is configured to receive written instructions for dispensing at least the first and second medicines $M_1$, $M_2$, preferably on or in the provided lines, tables, etc., as depicted in FIGS. 4-6. However, the kit 10 may be provided without any pre-printed or prepared sheets, and instead only be furnished with directions 20, as described below, which include instructions for preparing ordinary commercially-available paper sheets with treatment directions, as mentioned above and discussed in further detail below.

Furthermore, the directions 20 include instructions for preparing the kit 10 for use in treating a particular person (i.e., the child or infirm adult). Specifically, the directions 20 include at least instructions to attach the first indicator 12A to the first medicine $M_1$, to attach the second indicator 12B to the second medicine $M_2$, to transcribe instructions for dispensing the first medicine $M_1$ on a treatment instruction sheet $S_1$, and to transcribe instructions for dispensing the second medicine $M_2$ on the instruction sheet $S_1$ or on another treatment instruction sheet $S_2$. Such directions also preferably include directions to attach the preferred first index 18A to the instruction sheet $S_1$ and the second index 18A on the same sheet $S_1$ or on a different sheet $S_2$. Instead of including the indicators 12A, 12B, etc. with the treatment kit 10, the directions 20 may include instructions for forming each one of the indicators 12A, 12B, 12C, etc., for example from colored tape or commercially available stickers. Preferably, the directions 20 include at least one printed sheet 22 containing the instructions, as depicted in FIG. 1, but may alternatively be provided by an electronic storage device containing the instructions, for example a thumb drive, etc., or a printed sheet including a web address (i.e., a URL) or a QR code for accessing instructions online, or listing a mobile App which provides the instructions (no alternatives shown).

By having indicators 12A, 12B on the first and second medicines $M_1$, $M_2$ and corresponding indices 18A, 18B on the instruction sheet $S_1$, or sheets $S_1$ and $S_2$, the user of the kit 10 may readily select the appropriate medicine $M_1$, $M_2$ depending on the severity of a medical event, such as an asthma attack, an allergic reaction, a heart attack or other heart issue, etc. That is, when a medical event occurs, the user of the kit 10 first consults the instruction sheet $S_1$ or/and $S_2$, determines the level of severity by consulting the description and symptoms listed by the user on the one or more sheets $S_1$, $S_2$, etc. and then determines or recognizes the index 18A, 18B which corresponds to that severity level, and thereafter selects the appropriate medicine $M_1$ or $M_2$ by matching the indicator 12A, 12B on the medicine $M_1$, $M_2$ with the index 18A, 18B of the determined severity level.

Preferably, the first visual indicator 12A is at least a first color, for example yellow, and the second visual indicator 12B is at least a second color different than the first color, e.g., red. However, the first indicator 12A may alternatively be or also include a symbol, as depicted, such as an alphanumeric character (e.g., letter "A", number "1", etc.), a geometric shape, an ISO 7010 symbol, etc., and the second indicator 12B is instead or also include a different symbol of the same type as the first indicator 12A, but may otherwise be formed as a symbol of another desired type. As illustrated in this disclosure, such indicators 12 are only depicted as different symbols in the drawing figures as different colors cannot be readily shown. In any case, the indices 18A, 18B, etc. are preferably identical colors, symbols, etc. as the indicators 12A, 12B, etc., in order quickly match the required medicine $M_1$, $M_2$, etc., with the specific level of the medical condition.

That is, each index 18A, 18B, etc. is at least substantially identical to the corresponding indicator 12A, 12B; for example, if the first indicator 12A is a red colored sticker, or a red colored sticker with the letter "A", then the first index 18A should also be a red colored sticker or a red sticker with the letter "A". Preferably, the indicators 12 and the indices 18 are each formed as a separate adhesive sticker 19 having one or more selected colors and/or symbols, as discussed below, each provided on one or more backing sheets 21, as depicted in FIG. 1. However, the indicators 12 and/or the indices 18 may be formed in any other appropriate manner, such as printed tape, adhesive tabs, decals or in any other appropriate manner capable of being readily attached to the medicines M or/and to the instruction sheets S.

For example, if the treatment subject (i.e., a child or infirm adult) has an allergy with two potential levels of allergic reactions each requiring a separate medicine $M_1$ or $M_2$, for example, a first pill for a severe reaction and a second pill for a mild reaction, the kit 10 may be set up as follows. A first visual indictor 12A formed as a red sticker and/or with a symbol, for example, letter "A", may be attached to the first medicine $M_1$ and a second visual indicator 12B formed as a yellow sticker and/or with a different symbol, e.g., letter "B", may be attached to the second medicine $M_2$. Then, a first index 18A formed as a red adhesive sticker with a letter "A" may be attached to a treatment instruction sheet $S_1$ and appropriate directions written on the sheet $S_1$, such as "Give child one (1) pill from medicine bottle $M_1$ when child experiences wheezing, nausea, dizziness, or fainting and call 911". Also, a second index 18B formed as a yellow adhesive sticker with the letter "B" may be attached to the treatment instruction sheet $S_1$, or on a second instruction sheet $S_2$ (as shown), with directions such as "Give child one (1) pill from medicine bottle $M_2$ when child develops rash on arms or face".

Further, if the same allergic condition requires multiple medicines for each level of severity, such as a third medicine $M_3$ for severe reactions and a fourth medicine $M_4$ for mild reactions, the treatment kit 10 further comprises third and fourth visual indicators 12C, 12D, respectively, for example a letter "C" and a letter "D", as well as corresponding third and fourth indices 18C, 18D, respectively, for attachment to the appropriate instruction sheet $S_1$ or/and $S_2$. Also, the kit 10 may accommodate three or more medicines for a particular level of severity of the allergy, for example a fifth medicine $M_5$, such as an EpiPen 4 (FIG. 7), for severe allergic reactions, and therefore include a fifth indicator 12E (e.g., a letter "E") for attachment to the medicine $M_5$, and a corresponding fifth index 18E for attachment to one of the instruction sheets $S_1$ or $S_2$ (shown on sheet $S_1$).

Furthermore, the treatment kit 10 is preferably further configured to treat at least two different medical conditions. For example, if the same subject as discussed above has both the food allergy and asthma, the kit 10 preferably further includes at least a third holder 16 for retaining a third medicine M, at least a third indicator 12 and at least a third index 18. Specifically, with the treatment kit 10 described above, the kit 10 preferably further includes a sixth indicator 12F, for example a number "1", for attachment to a sixth medicine $M_6$, such as an asthma inhaler, and a corresponding sixth index 18F attachable to the one of the first and second treatment sheets $S_1$, $S_2$ or preferably to a third treatment sheet $S_3$, as shown. If likely to suffer different levels of asthmatic events or "attacks", the kit 10 preferably further includes at least a fourth holder 16 for retaining a fourth medicine M, a fourth indicator 12 and a fourth index 18. Specifically, with the above-described treatment kit 10, the kit 10 includes a seventh indicator 12G, such as a number "2", for attachment to a seventh medicine $M_7$, such as steroid tablets (e.g., prednisone), and a corresponding seventh indicator 18G attachable to the third treatment sheet $S_3$, as best shown in FIG. 6.

Figure 2:
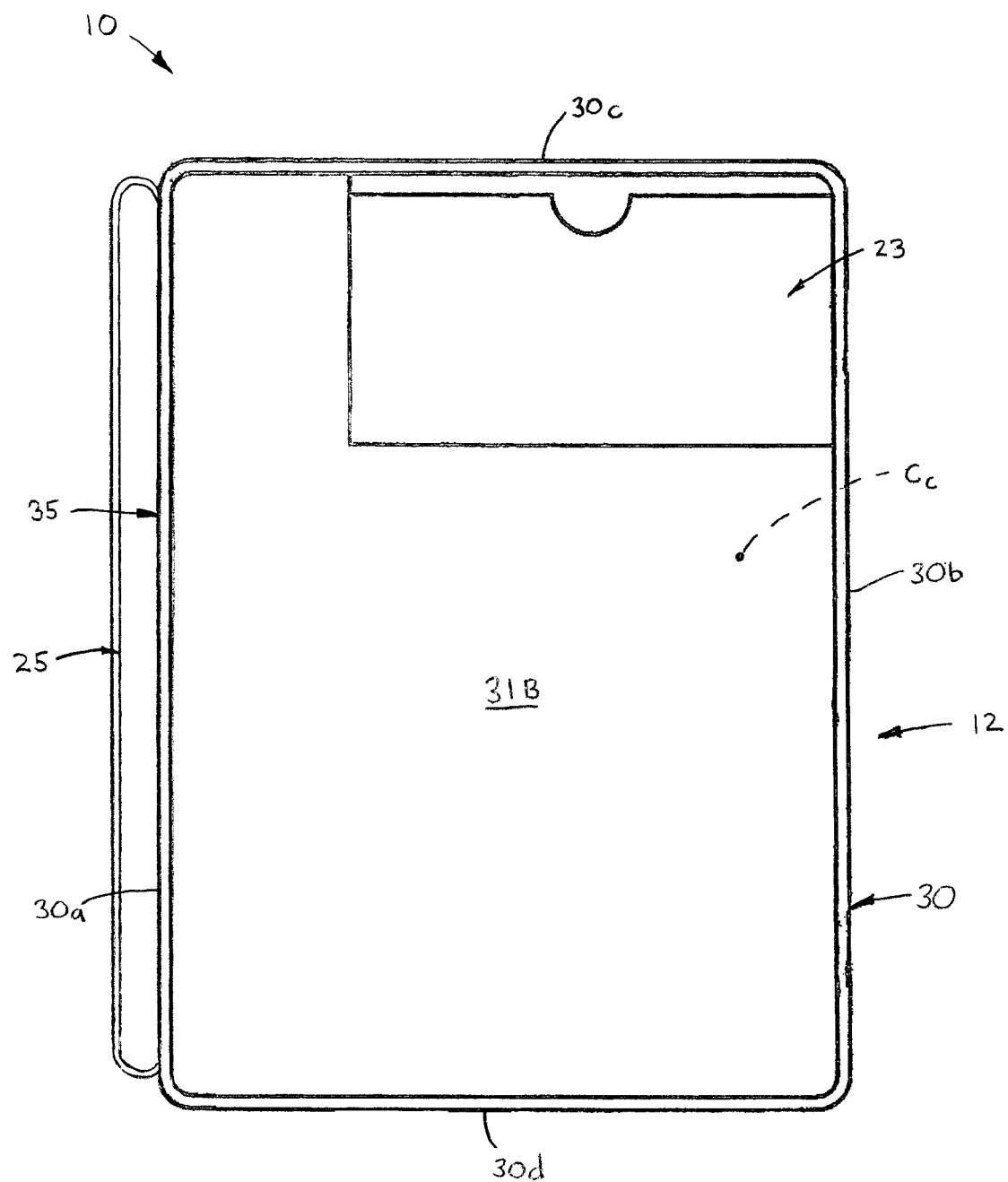
FIG. 2 is a side plan view of the treatment kit in a closed configuration.
Figure 3:
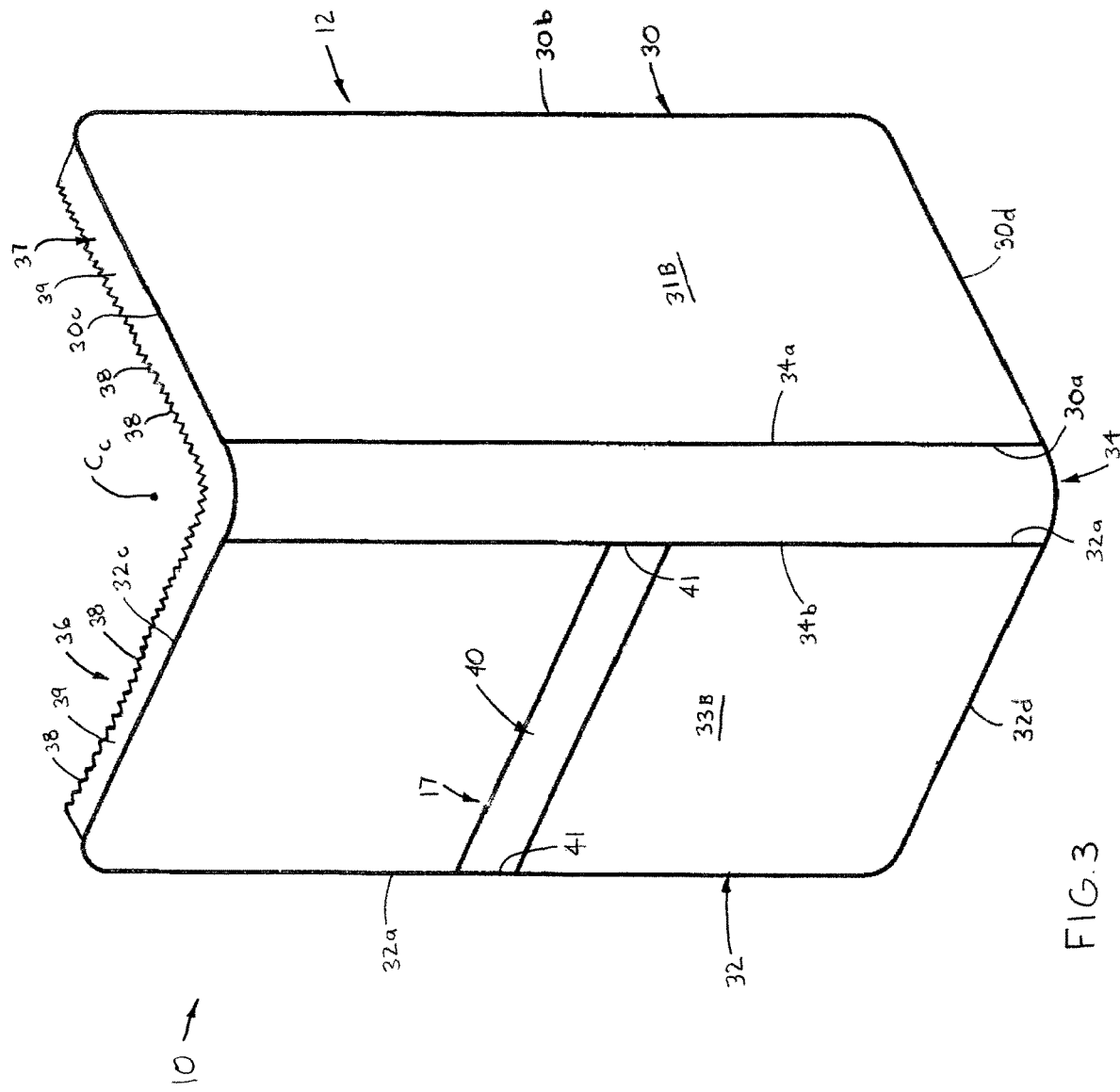
FIG. 3 is a rear perspective view of the treatment kit, shown in a partly open configuration.

Referring now to FIGS. 1-3, the case 12 is preferably a "soft" case made of fabric such as vinyl, nylon, etc. and formed in a generally rectangular solid shape that is sized to be carriable by or within a single human hand. The case 12 basically includes first and second panels 30, 32, a joint 34 pivotally coupling the two panels 30, 32 and a closure device 36 for releasably coupling the panels 30, 32. More specifically, each of the first and second panels 30, 32 is generally rectangular and has an inner longitudinal edge 30a, 32a, an opposing outer longitudinal edge 30b, 32b, two opposing lateral edges 30c, 30d and 32c, 32d extending between the longitudinal edges 30a, 30b and 32a, 32b, and opposing planar interior surfaces 31A, 33A and planar exterior surface 31B, 33B. Each one of the case panels 30, 32 is preferably formed of woven polymeric material, such as polyester, nylon, canvas, vinyl, neoprene, etc., reinforced by an interior sheet of a rigid polymeric material, such as rigid polyethylene. Preferably, the case 12 further includes an identification card holder 23 attached to the outer surface 31A of the first panel 32, as shown in FIG. 2, to permit the display of identifying information to associate the kit 10 with a specific person to be treated therewith.

Further, the joint 34 pivotally couples the inner longitudinal edge 30a of the first panel 30 with the inner longitudinal edge 32a of the second panel 32 so as to form a spine 35. Specifically, the joint 34 is preferably formed as a rectangular strip having a first longitudinal edge 34a connected to the first panel inner edge 30a by flexible polymeric material and a second longitudinal edge 34b connected to the second panel inner edge 32a by flexible polymeric material. However, the joint 34 may be formed in any other appropriate manner, such as for example, a plurality of pivotally interlocking hinge members (not shown). Also, the case 12 preferably further has a carry handle 25 attached to the outer surface of the spine 35, as depicted in FIG. 2.

Further, the closure device 36 releasably couples the outer longitudinal edge 30b of the first panel 30 with the outer longitudinal edge 32b of the second panel 32. As such, the interior chamber $C_C$, which is configured to store the medicines, medical devices, instructions sheets, etc., is defined between the first and second panels 30, 32 when the panel outer longitudinal edges 30b, 32b are coupled together, as indicated in FIGS. 2 and 3. Preferably, the closure device 36 is a zipper 37 that extends along and releasably couples each lateral edge 30c, 32c, each outer longitudinal edge 30b, 32b, and each lateral edge 30d, 32d. Specifically, the zipper 37 includes a plurality of teeth or elements 38 and two tape sections 39 connecting the teeth 37 with the edges of the panels 30, 32, as shown in FIG. 3, the tape sections 39 being sized such that the width of the zipper 37 is about equal to the spine 35 when the teeth 38 are connected. However, the closure device 36 may alternatively be formed as a snap button, a pair of hook and loop fasteners, or any other appropriate type of known closure mechanism appropriate for the case 12.

Referring now to FIGS. 1 and 4-8, each one of the medicine holders 16A, 16B, 16C, etc. is preferably formed by an elastic band 40 having opposing ends 40a, 40b each attached to the interior surface 31A of the first case panel 30 by one or more stitch lines 41. Preferably, the case 12 includes six of the holders 16, 16B, 16C, 16D, 16E, 16F each formed from a section 43 of a separate one of three elastic bands 40 spaced apart between the lateral edges 30c, 30d of the first panel 30. Each band section 43 is defined between the stitch lines 41 and is stretchable in a direction generally away from the panel 30 such that at least one medicine M (and possibly two medicines M) may be disposed between the band section 43 and the interior planar surface 31A, and thereafter retained by the elasticity of the band 40. However, one or more (or all) of the holders 16A-16F may be formed as a separate retainer clip, a pair of hook and loop fasteners (e.g., Velcro), a slot formed in the case 12 or any other appropriate manner (no alternatives shown). As shown in FIG. 3, the case 12 preferably has an exterior medicine holder 17 formed as an elastic band 40 with two ends 41 stitched to the exterior surface 33B of the second case panel 32, which is particularly suited to retaining a relative large medical item (none shown), such as an asthma inhaler spacer, that may otherwise occupy a substantial amount of the space within the case interior chamber $C_C$.

Furthermore, the case 12 preferably also includes an interior panel 44 providing a compartment 46 within the interior chamber $C_C$, which is sized to receive one or more medicines and/or at least one medical treatment device, such as a thermometer, etc. (none shown). The panel 44 is which is preferably formed as a flexible mesh panel 48 having three edges 48a, 48b and 48c attached to the interior surface 33A of the second panel 32 and a zipper 50 extending along another edge 48d to enable access and alternatively enclose the compartment 46. However, the panel 44 may be formed of a solid panel of an elastomeric material (e.g., vinyl) or the case 12 may be formed without any interior panels and instead include additional holders 16 disposed on or attached to the second panel interior surface 33A.

As shown in FIGS. 1 and 4-7, the sheet retainer 14 is preferably formed as a ring binder 54 including a plurality of ring clamps 56, most preferably two clamps 56, for engagement through openings $O_S$ in the treatment instruction sheets $S_1$, $S_2$, etc. That is, each clamp 56 is openable by pulling apart two halves (not indicated) of the clamp 56, to add or remove sheets S from the binder 54, and alternately closeable by pushing together the two clamp halves to retain the sheets $S_1$, $S_2$, etc. The ring binder 34 may be directly mounted to or disposed on an interior surface of the spine 35 by any appropriate means, such as riveting, adhesives, etc., as shown in FIGS. 1 and 3-7. However, the ring binder 34 is preferably mounted on a relatively thin base panel 57 that is coupled with the second panel 32 of the case 12 by sliding the base panel 57 through a slotted opening 60 and into a narrow cavity 58 formed in the second panel 32, such that the binder 34 is disposed on the second panel 32, as shown in FIG. 8.

Alternatively, as shown in FIG. 9, the sheet retainer 14 may be provided solely by the cavity 58 formed in the second panel 32, which is sized to receive a rigid sheet (e.g., formed of cardboard) of a pad (not shown) containing a plurality of instructions sheets $S_1$, $S_2$, $S_3$, etc. The cavity 58 is accessed by the slotted opening 60, as discussed above, such that the rigid sheet may be slided into the cavity 58 to loosely couple the pad with the case 12 generally adjacent to the spine 35. However, the sheet retainer 14 may be formed in any other appropriate manner that functions to retain instruction sheets within the case 12.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as generally defined in the appended claims.

We claim:

1. A portable medical kit for treatment of at least one medical condition of an individual, the condition having first and second levels of severity, the treatment kit comprising:
    a portable case having an interior chamber and at least two medicine holders each configured to retain a separate one of a first medicine and a second medicine within the chamber or at least one medicine holder configured to retain both of the first and second medicines within the chamber;
    a sheet retainer configured to couple at least one treatment instruction sheet with the case;
    a first visual indicator attachable to the first medicine and a second visual indicator attachable to the second medicine, the second indicator being readily visually distinguishable from the first indicator, or instructions to form the first indicator and the second indicator;
    at least one treatment instruction sheet coupleable with the sheet retainer and configured to receive written instructions for dispensing the first and second medicines;
    directions to attach the first indicator to the first medicine, to attach the second indicator to the second medicine, to transcribe instructions on the at least one treatment instruction sheet to dispense the first medicine when the individual experiences the first severity level of the condition, and to transcribe instructions on the at least one instruction sheet or another instruction sheet to dispense the second medicine when the individual experiences the second severity level of the condition;
    a first index attachable to the at least one instruction sheet and corresponding to the first indicator; and
    a second index attachable to the at least one instruction sheet or to another instruction sheet, the second index corresponding to the second indicator;
    wherein a user of the kit may readily select the appropriate one of the first medicine and the second medicine depending on the level of severity of the at least one medical condition by consulting the at least one treatment instruction sheet, determining which one of the first and second indices corresponds to the particular level of severity and matching the indicator on the medicine with the index of the determined severity level.

2. The treatment kit as recited in claim 1 wherein the directions include at least one sheet containing the instructions, an electronic storage device containing the instructions, and a sheet including a web address or QR code for accessing instructions online or identifying a mobile App.

3. The treatment kit as recited in claim 1 wherein:
    the first visual indicator includes one of a first color and a first symbol; and
    the second visual indicator includes a second color different than the first color when the first indicator includes a first color and the second visual indicator includes a second symbol different than the first symbol when the first indicator includes the first symbol.

4. The treatment kit as recited in claim 1 wherein one of:
    the first visual indicator includes a first color and the second visual indicator includes a second color different than the first color;
    the first visual indicator includes a first symbol and the second visual indicator includes a second symbol different than the second symbol.

5. The treatment kit as recited in claim 1 wherein the sheet retainer includes one of a ring binder device and a sleeve configured to receive a pad of paper.

6. The treatment kit as recited in claim 1 wherein the portable case further includes a third holder for retaining a third medicine for treating a medical condition different than the at least one medical condition.

7. The treatment kit as recited in claim 1 wherein:
    the portable case further has a third holder for a third medicine and a fourth holder for a fourth medicine; and
    the kit further comprises a third visual indicator attachable to the third medicine and a fourth visual indicator attachable to fourth medicine, each one of the first, second, third and fourth visual indicators being visually distinguishable from each other visual indicator.

8. The treatment kit as recited in claim 1 wherein each one of the medicine holders includes one of a retainer clip, a flexible loop, a pair of hook and loop fasteners and a slot formed in the case.

9. The treatment kit as recited in claim 1 wherein the case further includes an interior panel providing a compartment within the interior cavity, the compartment being sized to receive at least one of a third medicine and at least one medical treatment device.

10. The treatment kit as recited in claim 1 wherein the case includes:
    first and second panels, each case panel having inner and outer longitudinal edges and two lateral edges;
    a joint pivotably coupling the inner longitudinal edge of the first panel with the inner longitudinal edge of the second panel so as to form a spine; and
    a closure device for releasably coupling the outer longitudinal edge of the first panel with the outer longitudinal edge of the second panel, the interior cavity being defined between the first and second panels when the first and second panel outer longitudinal edges are coupled together.

11. The treatment kit as recited in claim 10 wherein the closure device includes one of zipper, a snap button and a pair of hook and loop fasteners.

12. The treatment kit as recited in claim 10 wherein:
    each one of the two medicine holders or the single medicine holder is attached to an interior surface of the case first panel; and
    the instruction retainer is disposed on an interior surface of the spine or on an interior surface of the second case panel.

13. The treatment kit as recited in claim 12 further comprising an interior panel disposable against an interior surface of the second panel and coupled with the second panel so as to define a compartment between the interior panel and the interior surface of the case second panel, the compartment being sized to receive at least one of a third medicine and at least one medical treatment device.

14. The treatment kit as recited in claim 1 wherein the portable case is sized to be carriable by or within a single human hand.

* * * * *